United States Patent [19]

Welstead, Jr. et al.

[11] 4,045,576
[45] Aug. 30, 1977

[54] ANTI-INFLAMMATORY METHODS USING 2-AMINO-3-(5- AND 6-)BENZOYLPHENYLACETIC ACIDS, ESTERS AND METAL SALTS THEREOF AND THE COMPOUNDS

[75] Inventors: William J. Welstead, Jr.; Henry W. Moran, both of Richmond, Va.

[73] Assignee: A. H. Robins Company, Incorporated, Richmond, Va.

[21] Appl. No.: 604,371

[22] Filed: Aug. 13, 1975

Related U.S. Application Data

[63] Continuation-in-part of Ser. No. 487,499, July 11, 1974, abandoned, which is a continuation-in-part of Ser. No. 354,625, April 25, 1973, abandoned, which is a continuation-in-part of Ser. No. 254,285, May 17, 1972, abandoned.

[51] Int. Cl.[2] .................... A01N 9/20; C07C 101/447
[52] U.S. Cl. ........................ 424/309; 260/471 R; 260/517; 424/319; 260/326.47; 260/326.16
[58] Field of Search .............. 260/471 R, 517; 424/309, 319

[56] References Cited

U.S. PATENT DOCUMENTS 3,828,093  8/1974  Bays et al. .............. 260/471 R X

FOREIGN PATENT DOCUMENTS 2,324,768  11/1973  Germany ................ 260/471 R

*Primary Examiner*—Anton H. Sutto

[57] ABSTRACT

Novel 2-amino-3-(5- and 6-)benzoylphenylacetic acids, esters and metal salts of the formula:

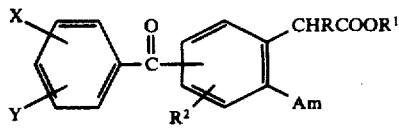

wherein R is hydrogen or lower alkyl, $R^1$ is hydrogen, lower-alkyl, sodium or potassium, $R^2$ is hydrogen, halogen or lower alkoxy, X is hydrogen, lower alkyl, halogen, nitro or trifluoromethyl, Y is hydrogen, lower alkyl, halogen, nitro or trifluoromethyl, and Am is primary amino ($-NH_2$) methylamino or dimethylamino. The compounds are prepared by hydrolysis of 4-(5- and 7-)benzoylindolin-2-ones to give the 2-amino-3-(5- and 6-)benzoylphenylacetic acids wherein amino is primary amino. The free acids are converted to the esters and metal salts. The calcium and magnesium salts are disclosed and are within the scope of the present invention. The compounds have anti-inflammatory activity, are effective in lowering the cholesterol levels in hyperlipemic rats and inhibit blood platelet aggregation.

47 Claims, No Drawings

ANTI-INFLAMMATORY METHODS USING 2-AMINO-3-(5- AND 6-)BENZOYLPHENYLACETIC ACIDS, ESTERS AND METAL SALTS THEREOF AND THE COMPOUNDS

This application is a continuation-in-part application of copending application Ser. No. 487,499 filed July 11, 1974, now abandoned which is a continuation-in-part application of copending application Ser. No. 354,625 filed Apr. 25, 1973, now abandoned, which application is a continuation-in-part application of copending application Ser. No. 254,285 filed May 17, 1972, now abandoned.

The present invention relates to novel substituted phenylacetic acids, esters, alkali metal salts and alkaline earth metal salts thereof and is more particularly concerned with certain 2-amino-3-(5- and 6-)benzoylphenylacetic acids, esters, alkali metal salts and alkaline earth metal salts, compositions thereof, methods for the production thereof and use of the same.

The invention is especially concerned with 2-aminophenylacetic acids, esters and alkali metal salts having the formula:

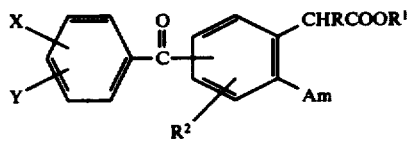

(I)

wherein;

R is hydrogen or lower alkyl, $R^1$ is hydrogen, lower alkyl or alkali metal cation, $R^2$ is hydrogen, halogen or lower alkoxy, X is hydrogen, lower alkyl, halogen, nitro or trifluoromethyl, Y is hydrogen, lower alkyl, halogen, nitro, or trifluoromethyl, and Am is primary amino (—NH$_2$), methylamino or dimethylamino.

The preferred alkali metal salts of Formula I are the sodium and potassium salts. The salts possess anti-inflammatory activity and are useful intermediates for the preparation of the esters of Formula I.

The present invention also includes the alkaline earth metal salts of Formula I-A. The preferred salts are the calcium and magnesium salts.

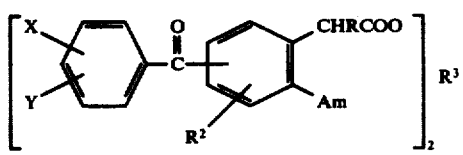

(I-A)

In Formula I-A, R, $R^2$, X, Y and Am have the values given hereinabove and $R^3$ is an alkaline earth metal, preferably calcium or magnesium.

The novel compounds of Formulae I and I-A possess valuable pharmacological properties and are useful as pharmaceutical agents. The compounds exhibit anti-inflammatory activity, lower cholesterol levels in hyperlipemic rats and inhibit blood platelet aggregation.

The anti-inflammatory activity was demonstrated using a modification of the Evans Blue-Carrageenan Pleural Effusion Assay of Sancilio, L. F., J. Pharmacol. Exp. Ther. 168, 199-204 (1969).

The prior art (South African Patent 68/4682) discloses 4-amino-3-benzoylphenylacetic acid, m.p. 135°-7° C. The compound was prepared and tested for anti-inflammatory activity by the method of Sancilio referred to immediately hereinabove. Comparative test data shows that 2-amino-3-benzoylphenylacetic acid, sodium 2-amino-3-benzoylphenylacetate and 2-amino-6-benzoylphenylacetic acid respectively have about 39 times, 48 times and 3 times the activity of the prior art 4-amino-3-benzlylphenylacetic acid.

It is therefore an object of the present invention to provide novel compounds and compositions. Another object is to provide methods for the preparation of the novel compounds. A still further object is to provide a novel method for the treatment of a living animal body and especially mammalian bodies for purposes of alleviating inflammation, reducing cholesterol levels and inhibiting blood platelet aggregation with a minimum of undesirable side effects. Additional objects will be apparent to one skilled in the art and still other objects will become apparent hereinafter.

In the definition of symbols in the formulas hereof and where they appear elsewhere throughout this specification, the terms have the following significance.

The term "lower alkyl" as used herein includes straight and branched chain radicals of up to six carbons inclusive, preferably no more than four carbon atoms and is exemplified by such groups as methyl, ethyl, propyl, isopropyl, butyl, sec. butyl, tertiary butyl, amyl, isoamyl and hexyl. The term "lower alkoxy" has the formula -O-lower alkyl.

The term "halogen" when referred to herein is preferably but not necessarily a halogen of atomic weight less than eighty.

The substituents which can be attached to the monosubstituted benzoyl radical and the disubstituted benzoyl radical can be a lower alkyl, halogen, nitro or trifluoromethyl radical or a combination thereof, said monosubstituted and disubstituted benzoyl radicals therefor including but not being limited to lower alkyl benzoyl, halobenzoyl such as chlorobenzoyl, bromobenzoyl and fluorobenzoyl, nitrobenzoyl and trifluoromethylbenzoyl, 3,5-dichlorobenzoyl, 2,4-dichlorobenzoyl, 3-trifluoromethyl-4-chlorobenzoyl, 2,4-dimethylbenzoyl, 3,5-dimethylbenzoyl, 3-nitro-4-chlorobenzoyl or 2-methyl-4-chlorobenzoyl, 3-methoxy-4-chlorobenzoyl or 3,4-methylenedioxybenzoyl.

When used hereinafter the term "benzoyl" refers to the unsubstituted benzoyl radical, the monosubstituted benzoyl radical or the disubstituted benzoyl radical.

METHOD OF PREPARATION

The preparation of the novel 2-amino-3-(5- and 6-)benzoylphenylacetic acids (I) of the present invention may be accomplished by hydrolysis of novel 4-(5- and 7-)benzoylindolin-2-ones (II) in aqueous basic solution following by neutralization of the basic reaction mixture. The reaction sequence is illustrated by the following:

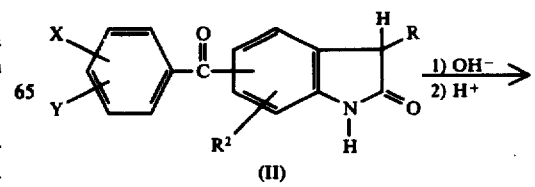

(II)

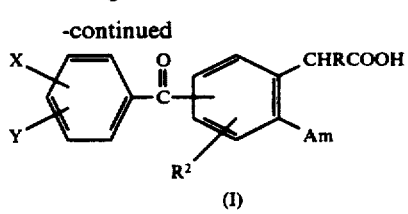

wherein R, R², X and Y are as defined hereinabove and Am is —NH₂.

The hydrolysis of an indolin-2-one (II) is carried out in dilute aqueous base as, for example, 3N sodium hydroxide solution, for a period of from about 0.5 hour to about 1.0 hour. The hydrolysis may be run in an inert atmosphere using nitrogen. The hydrolysis mixture may be filtered to remove base-insoluble materials and the pH of the basic solution is adjusted to pH 6-pH 7 by the addition of a weak organic acid such as glacial acetic acid or a dilute mineral acid such as hydrochloric acid. When (I) is a 2-amino-5-benzoylphenylacetic acid or a 2-amino-6-benzoylphenylacetic acid the product can be readily recrystallized from a suitable solvent. When (I) is a 2-amino-3-benzoylphenylacetic acid, recrystallization may result in partial cyclization to the precursor 7-benzoylindolin-2-one (II). Therefore, in the preparation of a 2-amino-3-benzoylphenylacetic acid (I) the product is preferably not recrystallized and is isolated by careful acidification of the filtered basic hydrolysis mixture.

The lower alkyl esters of Formula I are preferably prepared from the acids which are converted to an alkali metal salt, preferably the sodium or potassium salt which is isolated, dried and then reacted in a suitable solvent as, for example, dimethylformamide, with an alkyl halide, preferably an alkyl iodide to furnish the desired ester.

The compound of Formula I wherein Am is dimethylamino, is prepared by reacting a 2-aminophenylacetic acid of Formula I wherein Am is —NH₂ with formaldehyde and sodium cyanoborohydride in a solvent such as acetonitrile under mildly acidic conditions as provided by the use of glacial acetic acid.

The starting materials for the process of the present invention are the appropriately substituted 4-(5- and 7-)benzoylindolin-2-ones (II). The 5-benzoylindolin-2-ones can be prepared by reacting an indolin-2-one of Formula III with a benzoyl chloride in the presence of aluminum chloride to give an indolin-2-one of Formula II.

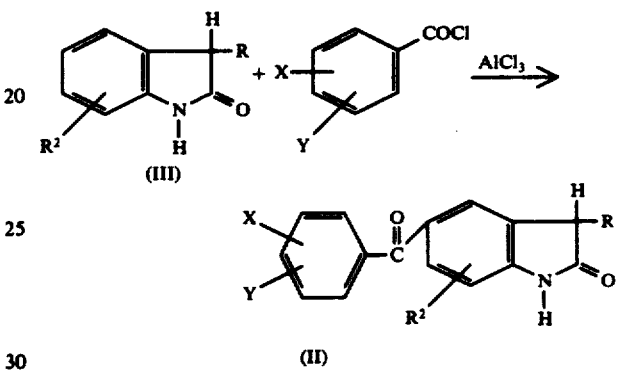

The indolin-2-ones (III) are either commercially available or they can be prepared by methods known to the art such as are disclosed by Wenkert et al., J. Am. Chem. Soc. 81, 3763–3768 (1959).

The 7-benzoylindolin-2-ones of Formula II are prepared by the following reaction sequence.

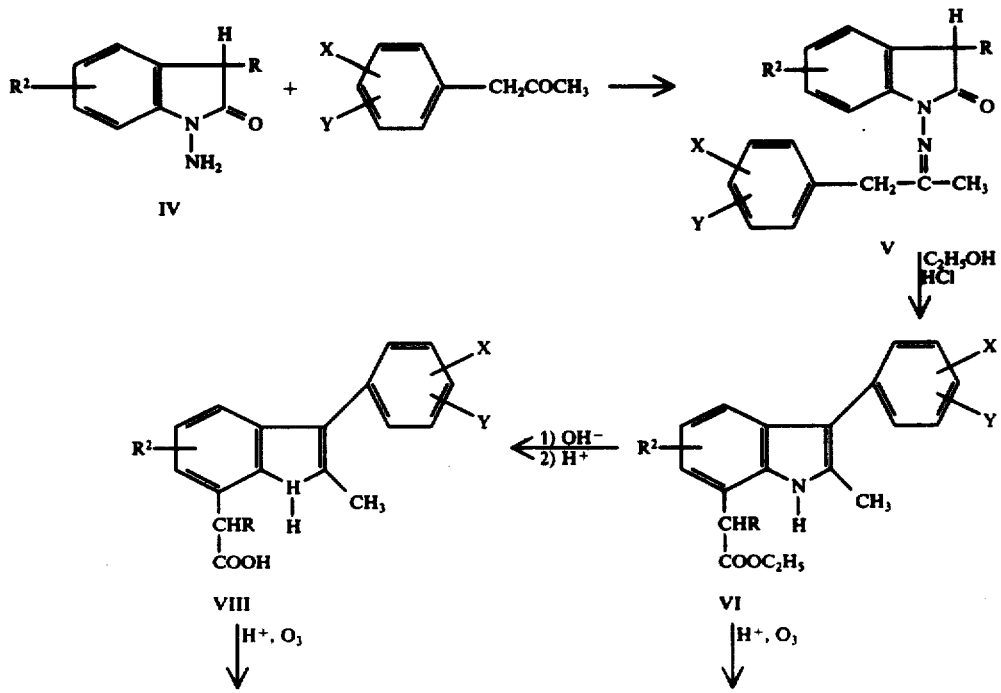

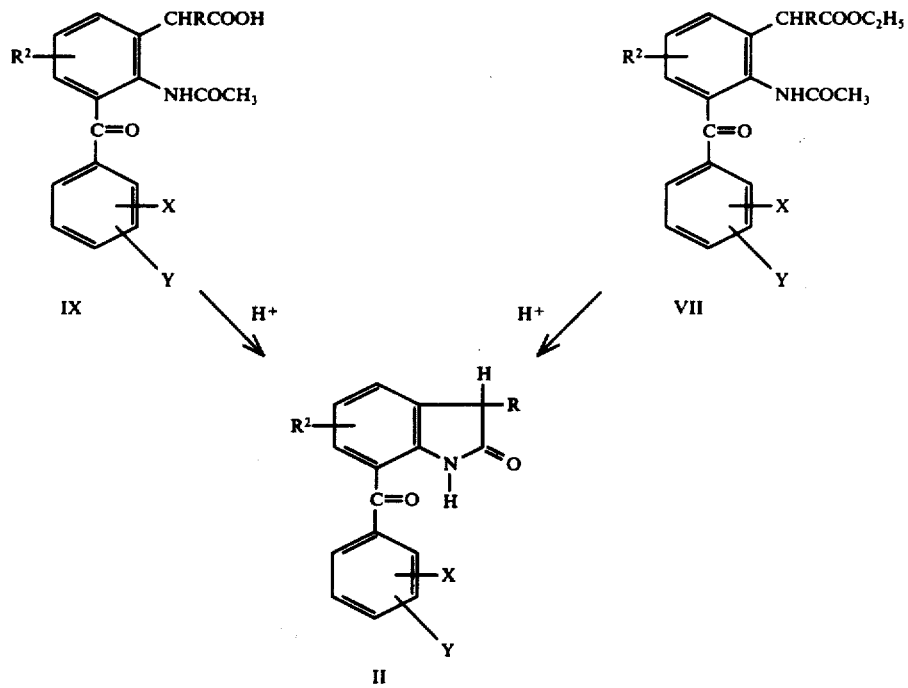

The 1-aminoindolin-2-one starting materials (IV) can be prepared by suitable methods known to the art such as are disclosed by Baumgarten et al., J. Am. Chem. Soc. 82, 3977-82 (1960). The 1-aminoindolin-2-one (IV) is reacted with an appropriately substituted phenylacetone to give a 1-(α-methylphenethylindenimino)indolin-2-one (V) which is cyclized in ethanolic hydrogen chloride to an ethyl α-(2-methyl-3-phenylindol-7-yl) acetate (VI). The indolylester is treated with ozone in acetic acid solution to give an ethyl 2-acetamido-3-benzoylphenylacetate (VII) which is hydrolyzed and cyclized in dilute mineral acid to a 7-benzoylindolin-2-one (II).

Alternatively, an ethyl α-(2-methyl-3-phenylindol-7-yl) acetate (VI) is hydrolyzed in aqueous basic solution to an α-(2-methyl-3-phenylindol-7-yl) acetic acid (VIII) which is treated with ozone in acetic acid solution to give a 2-acetamido-3-benzoylphenylacetic acid (IX). The acid is hydrolyzed and cyclized in dilute acid to the 7-benzoylindolin-2-one (II).

Compounds of Formula II wherein R² is methoxy are prepared by catalytic reduction of 7-carboxy-5-methoxyisatin, a known compound prepared by a modification of the procedure of Cragoe, E. J. et al., J. Org. Chem. 18, 561 (1953), to 7-carboxy-5-methoxyindolin-2-one and reaction of the latter compound with phenyllithium.

Compounds of Formula II wherein R² is chlorine are prepared by reacting the known 5-chloroindolin-2-one with a benzoyl chloride in the presence of aluminum chloride.

The 4-(5- and 7-)benzoylindolin-2-ones (II) can also be prepared from appropriately substituted aminobenzophenones (X) by the following reaction sequence, wherein R, R¹, R², X and Y have the values hereinabove defined. The reaction conditions employed are more fully set forth hereinafter in the specific preparations which follow.

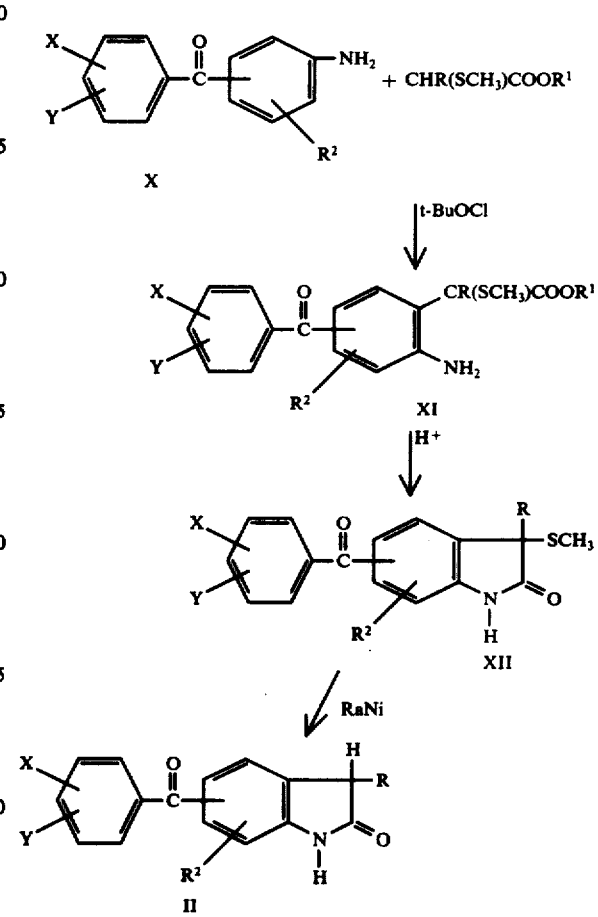

PREPARATION 1

5-Benzoylindolin-2-one.

A stirred slurry of 66 g. (0.5 mole) of aluminum chloride and 42.5 g. (0.3 mole) of benzoyl chloride was heated to 150° C. and then 133 g. (0.1 mole) of indolin-2-one was slowly added at a rate so that the temperature of the stirred reaction mixture was maintained at 180°–185° C. After addition the reaction mixture was stirred for five minutes at 185° C., cooled and poured into ice water. The 5-benzoylindolin-2-one which precipitated was collected and recrystallized from methanol; it melted at 204°–205° C. The yield was 17.5 g. (73%).

Analysis: Calculated for $C_{15}H_{11}N_1O_2$: C,75.94; H,4.67; N,5.90 Found: C,75.76; H,4.69; N,5.82.

PREPARATION 2

5-Benzoyl-3-methylindolin-2-one.

When, in the procedure of Preparation 1, an equal molar amount of 3-methylindolin-2-one is used in place of indolin-2-one, there is obtained 5-benzoyl-3-methylindolin-2-one.

PREPARATION 3

1-(α-Methylphenethylidenimino)indolin-2-one.

A mixture of 10 g. (0.07 mole) of 1-aminoindolin-2-one and 9.05 g. (0.07 mole) of phenylacetone in 65 ml. of absolute ethanol was heated until all the 1-aminoindolin-2-one dissolved. The solution was treated with 0.5 ml. of acetic acid and heated on a steam bath an additional 15 minutes. After cooling, the product was filtered off and the filtrate was treated with water. The additional product which precipitated from the filtrate was combined with the original material and recrystallized from absolute alcohol; yield 16 g. (90%); m.p. 102°–104° C.

Analysis: Calculated for $C_{17}H_{16}N_2O$: C,77.25; H,6.10; N,10.60 Found: C,77.26; H,6.16; N,10.58

PREPARATION 4

Etyl α-(2-methyl-3-phenylindol-7-yl)acetate.

A solution of ethanolic hydrogen chloride was prepared by bubbling dry hydrogen chloride into 100 ml. of absolute ethanol until the solution began to boil. At this point 10 g. (0.04 mole) of 1-(α-methylphenethylidenimino)indolin-2-one was added and the mixture was stirred for 30 minutes. Additional hydrogen chloride was bubbled into the hot mixture until thin layer chromatography showed no starting material remained. The reaction was allowed to cool and the solid which separated from the cooled reaction mixture was filtered off and was shown to be 1-aminoindolin-2-one. The filtrate was concentrated and the residual brown oil was shown by nuclear magnetic resonance to be a mixture of phenylacetone and product. The mixture was distilled at 165°–175° C. (0.5 mm.); the oily distillate solidified upon cooling. The solid was recrystallized from ligroin to give ethyl α-(2-methyl-3-phenylindol-7-yl)acetate which melted at 108°–109° C. and weighed 2.2 g. (21%).

Analysis: Calculated for $C_{19}H_{19}NO_2$: C,77.79; N,6.53; N,4.77 Found: C,77.60; H,6.54; N,4.77

PREPARATION 5

α-(2-Methyl-3-phenylindol-7-yl)acetic acid.

To a solution of 8 g. of potassium hydroxide in 100 ml. of water was added 6 g. (0.02 mole) of ethyl α-(2-methyl-3-phenylindol-7-yl)acetate. The mixture was refluxed for two hours. The cooled reaction mixture was filtered and the filtrate diluted with an equal volume of water. Acidification of the basic solution with 3N hydrochloric acid gave α-(2-methyl-3-phenylindol-7-yl)acetic acid which was recrystallized from benzene; yield 3 7 g. (67%); m.p. 165° C. (dec.).

Analysis: Calculated for $C_{17}H_{15}NO_2$: C,76.96; H,5.70; N,5.28 Found: C,77.09; H,5.70; N,5.22.

PREPARATION 6

Ethyl 2-acetamido-3-benzoylphenylacetate.

A solution of 5 g. (0.017 mole) of ethyl α-(2-methyl-3-phenylindol-7yl)acetate and 75 ml. of acetic acid was treated with ozone for 25 minutes. After ozonation, the acetic acid solution was diluted with water and extracted with ether. The ether extracts were washed with water, 5% sodium carbonate, dried (magnesium sulfate) and concentrated. Recrystallization from isopropanol gave 2.6 g. (47%) of product which melted at 133°–134° C.

Analysis: Calculated for $C_{19}H_{19}NO_4$: C,70.14; H,5.89; N,4.30 Found: C,69.95; H,5.99; N,4.12.

PREPARATION 7

2-Acetamido-3-benzoylphenylacetic Acid.

A solution of 2 g. of α-(2-methyl-3-phenylindol-7-yl)acetic acid in 60 ml. of acetic acid was treated with ozone for 15 minutes. The reaction mixture was treated with 10 ml. of water and allowed to evaporate overnight. The residue (1.7 g.) was recrystallized from isopropanol; yield 1.6 g. (71%); m.p. 188°–190° C.

Analysis: Calculated for $C_{17}H_{15}NO_4$: C,68.68; H,5.08; N,4.71 Found: C,68.33; H,5.11; N,4.58.

PREPARATION 8

7-Benzoylindolin-2-one.

Method A

A mixture of 2.5 g. (0.0077 mole) of ethyl 2-acetamido-3-benzoylphenylacetate in 50 ml. of 3N hydrochloric acid was refluxed for one hour. The reaction mixture was filtered and the filtrate was poured into a mixture of ice and water. The precipitate was collected and recrystallized from acetone; yield 1 g. (55%); m.p. 154° C.

Analysis: Calculated for $C_{15}H_{11}NO_2$: C, 75.94; H, 4.67; N,5.90 Found: C,75.84; H,4.76; N,5.78.

Method B

A solution of 1.3 g. (0.0044 mole) of 2-acetamido-3-benzoylphenylacetic acid in 15 ml. of 3N hydrochloric acid and 15 ml. of acetic acid was refluxed for three hours. The cooled solution was poured into ice water and the 7-benzoylindolin-2-one which precipitated was collected and dried.

PREPARATION 9

Other 5-benzoylindolin-2-ones. -5-(p-chlorobenzoyl)-indolin-2-one, 5-(o-fluorobenzoyl)indolin-2-one, 5-(p-methoxybenzoyl)indolin-2-one and 5-(m-trifluoromethylbenzoyl)indolin-2-one are prepared in the manner of Preparation 1 from indolin-2-one and the corresponding substituted benzoyl chloride.

PREPARATION 10

Other 1-(α-methylphenethylidenimino)indolin-2-ones. -1-(α-methyl-p-chlorophenethylidenimino)indolin-2-one, 1-(α-methyl-o-fluorophenethylidenimino)indolin-2-one and 1-(α-methyl-m-trifluoromethylphenethylidenimino)indolin-2-one are prepared in the same manner of Preparation 2 from 1-aminoindolin-2-one and the corresponding substituted phenylacetone.

PREPARATION 11

Other ethyl α-(2-methyl-3-phenylindol-7-yl)acetates. -ethyl α-[2-methyl-3-(p-chlorophenyl)indol-7-yl]acetate, ethyl α-[2-methyl-3-(o-fluorophenyl)indol-7-yl]acetate and ethyl α-[2-methyl-3-(m-trifluoromethylphenyl)indol-7-yl]acetate are prepared in the same manner of Preparation 3 from the corresponding 1-(α-methylphenethylidenimino)indolin-2-one.

PREPARATION 12

Other α-(2-methyl-3-phenylindol-7-yl)acetic acids. -α-[2-methyl-3-(p-chlorophenyl)indol-7-yl]acetic acid, α-[2-methyl-3-(o-fluorophenyl)indol-7-yl]acetic acid and α-[2-methyl-3-(m-trifluoromethylphenyl)indol-7-yl]acetic acid are prepared in the same manner of Preparation 4 from the corresponding ethyl α-(2-methyl-3-phenyl-indol-7-yl)acetate.

PREPARATION 13

Other ethyl 2-acetamido-3-benzoylacetates. -ethyl 2-acetamido-3-(p-chlorobenzoyl)phenylacetate, ethyl 2-acetamido-3-(o-fluorobenzoyl)phenylacetate and ethyl 2-acetamido-3-(m-trifluoromethylbenzoyl)phenylacetate are prepared in the same maner of Preparation 5 by ozonation of the corresponding ethyl α-(2-methyl-3-phenylindol-7-yl)acetates.

PREPARATION 14

Other 2-acetamido-3-benzoylphenylacetic acids. -2-acetamido-3-(p-chlorobenzoyl)phenylacetic acid, 2-acetamido-3-(o-fluorobenzoyl)phenylacetic acid and 2-acetamido-3-(m-trifluoromethylbenzoyl)phenylacetic acid are prepared in the same manner of Preparation 6 by ozonation of the corresponding α-(2-methyl-3-phenylindol-7-yl)acetic acids.

PREPARATION 15

Other 7-benzolindolin-2-ones. -7-(p-chlorobenzoyl)indolin-2-one, 7-(o-fluorobenzoyl)indolin-2-one and 7-(m-trifluoromethylbenzoyl)indolin-2-one are prepared in the same manner of Preparation 7 by cyclization of the corresponding ethyl 2-acetamido-3-benzoylphenylacetate or 2-acetamido-3-benzoylphenylacetic acid.

PREPARATION 16

7-Benzoyl-5-chloroindolin-2-one.

A mixture of 162.5 g. (1.08 mole) of benzoyl chloride and 260 g. of aluminum chloride (1.80 mole) heated to 200° C. with stirring was treated with 65 g. (.360 mole) of recrystallized 5-chloroindolin-2-one. This mixture was stirred 15 min. and poured over ice. The resulting precipitate was triturated with boiling water and then chloroform. The chloroform solution was washed with 5% sodium bicarbonate, water, dried over sodium sulfate, and stripped to yield approximately 55 g. of a glossy solid. This material was then triturated with hot methanol and the methanol evaporated under vacuum to yield approximately 20 g. of a solid yellow material. Extraction of a benzene solution of this material removed any starting 5-chloroindoline-2-one present and after washing with water and drying the benzene yielded on evaporation 3 g. of a blue-gray material. Trituration of this material with room temperature methanol gave a residue which on recrystallization from methanol yielded 2.5 g. of a tan solid identified as product, m.p. 186°-187° C.

Analysis: Calc'd for $C_{15}H_{10}ClNO_2$: C,66.31; H,3.71; N,5.16 Found: C,66.27; H,3.83; N,5.07.

PREPARATION 17

5-Methoxy-7-benzoylindolin-2-one.

A suspension of 1.0 g. (4.9 mole) of 5-methoxy-7-carboxyindolin-2-one in 20 ml. of tetrahydrofuran was treated dropwise with 12 ml. of commercially prepared phenyllithium solution (2.3 molar ether: benzene; 0.28 moles). After stirring for two hours the reaction mixture was poured into water and extracted several times with ethyl ether and benzene. The combined extracts were washed with water, dried over sodium sulfate and concentrated using a rotary evaporator to a solid residue which on recrystallization from acetone-water gave 259 mg. (21%) of a yellow powder which melted at 154° C.

PREPARATION 18

4-Benzoyl-3-methylthioindolin-2-one.

A solution of 30.6 (0.152 mole) of 3-aminobenzophenone in 160 ml. of methylene chloride was cooled to −78° C. in a dry ice/acetone bath and treated dropwise under a nitrogen atmosphere with a solution of 16.5 g. (0.152 mole) of t-butylhypochlorite in 60 ml. of methylene chloride. After stirring for 1 hr. after addition was complete, thin layer chromatography showed no starting material. A solution of 20.2 g. (0.152 mole) of ethyl α-(methylthio)acetate in 60 ml. of methylene chloride was added dropwise and stirring continued at −78° C. for 2.5 hr. A solution of 15.4 g. (0.152 mole) of triethylamine in 60 ml. of methylene chloride was added dropwise at −78° C. and the reaction mixture allowed to warm to room temperature while stirring for 16 hr. (overnight). The dark brown solution was treated with 100 ml. of 3N hydrochloric acid and stirred for 3 hrs. at room temperature. Precipitation of a tan solid began after 15–30 minutes. Filtration gave 18.5 g. of solid, m.p. 224°-228° C. (dec.) The layers of the filtrate were separated, the organic phase dried over magnesium sulfate, evaporated under reduced pressure, and the residue triturated in isopropyl ether (25 g.). The gummy solid was triturated in cold methanol to give 8.3 g. of product, m.p. 222°-225° C. (dec.). The total yield was 26.8 g. (62%). A 7.0 g. sample recrystallized from methanol weighed 5.6 g. and melted at 235°-237° C. (dec.).

Analysis: Calc'd for $C_{16}H_{13}NO_2S$: C,67.823; N,4.625; N,4.943 Found: C,67.86; N,4.71; N,4.85.

PREPARATION 19

7-(4-Chlorobenzoyl)-3-methylthioindolin-2-one.

A solution of 23.1 g. (0.1 mole) of 2-amino-4'-chlorobenzophenone in 400 ml. of methylene chloride was cooled to −65° C. and treated dropwise with 12.4 g. (0.1 mole) of t-butyl hypochlorite. After 15 min., 13.4 g. of ethyl α-(methylthio)-acetate (0.1 mole) was added dropwise maintaining −65° C. temperature. After 1½ hr. 10.1 g. of triethylamine (0.1 mole) was added and the reaction mixture allowed to come to room temperature. The solution was then washed with water and stripped. The residue was taken into methanol and brought to reflux at which time 1N hydrochloric acid was added and the resulting mixture refluxed overnight. The mixture was cooled, resulting precipitate filtered off and recrystallized from toluene, giving 10 g. of a cream colored solid. The product (33% yield) melted at 186°-188° C.

Analysis: Cald'd for $C_{16}H_{12}ClNO_2S$: C,60.47; H,3.81; N,4.41 Found: C,60.29; H,3.76; N,4.43.

PREPARATION 20

7-Benzoyl-3-methyl-3-metylthioindolin-2-one.

A stirred solution of 3.94 g. (0.02 mole) of 2-aminobenzophenone in methylene chloride at −65° C. was treated with 2.16 g. (0.02 mole) of t-butylhypochlorite. After 15 min. 2.96 g. ethyl α-(methylthio)propionate was added dropwise and stirring continued for 1 hr. At the end of this time 2.02 g. of triethylamine (0.02 mole) was added dropwise and the reaction solution was allowed to warm to room temperature. This was followed by treatment with 1N hydrochloric acid and stirred for 15 min. The methylene chloride solution was then separated and stripped under vacuum. The yellow oil residue was triturated with isopropyl ether and 3 g. of a yellow solid was filtered off (51%). Recrystallization from absolute ethanol gave a cream color solid, m.p. 135°-137° C.

Analysis: Calc'd for $C_{17}H_{15}NO_2S$: C,68.66; H,5.08; N,4.71 Found: C,68.54; H,5.08; N,4.63.

PREPARATION 21

7-Benzoyl-3-methylthioindolin-2-one.

A solution of 300 g. (1.52 mole) of 2-aminobenzophenone in 4 liters of methylene chloride was chilled to −40° C. and then treated with 204 g. (1.52 mole) of the ethyl α-(methylthio)acetate dissolved in 5 liters of methylene chloride. The reaction mixture was then cooled to −65° C. and treated dropwise with 500 ml. of a methylene chloride solution containing 164 g. (1.52 mole) of t-butylhypochlorite. After addition was complete, stirring was continued for 2 hr. at −70° treated with 182 g. (1.8 mole) of triethylamine and allowed to come to room temperature overnight. The methylene chloride solution was washed twice with 3 liters of ice water followed by drying over sodium sulfate and concentrating the dried solution to a yellow oil under reduced pressure. The oil was taken into 1.5 liters of methanol treated with 1 liter of 1N hydrochloric acid and refluxed for 2 hrs. After cooling in an ice bath 343 g. (79.9%) of crude produce was recovered after filtering and drying. Two recrystallizations from toluene gave creamy white flakes; m.p. 130° C.

Analysis: Calc'd for $C_{16}H_{13}NO_2S$: C,67.82; H,4.62; N,4.97 Found: C,68.06; H,4.68; N,4.87

PREPARATION 22

4-Benzoylindolin-2-one.

A stirred suspension of 7.0 g. (0.0248 mole) of 4-benzoyl-3-methylthioindolin-2-one in 400 ml. of tetrahydrofuran was treated portionwise under a nitrogen atmosphere with 35.0 g. of Raney nickel over a 2.5 hr. period. The reaction mixture was stirred for 1.5 hr. after addition was complete and the catalyst removed by filtration. The filter cake was washed well with tetrahydrofuran and methylene chloride and the filtrate evaporated under reduced pressure. The residue (5.6 g.) was recrystallized from methanol and gave 4.45 g. (76%) of product m.p. 210°-212° C.

Analysis: Calc'd for $C_{15}H_{11}NO_2$: C,75.937; H,4.673; N,5.904 Found: C,75.85; H,4.59; N,5.92.

PREPARATION 23

7-(4-Chlorobenzoyl)indolin-2-one.

A stirred solution of 9 g. (0.028 mole) of 7-(4-chlorobenzoyl)-3-methylthioindolin-2-one in 180 ml. of tetrahydrofuran was treated over a two-hour period with 45 g. of a commercial Raney nickel water suspension. After the addition was complete the mixture was filtered. A drop of concentrated hydrochloric acid was added to the filtrate which removed some color and the resulting solution was then stripped under water pump vacuum the yield a cream color material. Recrystallization from toluene gave needles, (93% yield); the material sintered at 177° C. and melted at 186° C.

Analysis: Calc'd for $C_{15}H_{10}ClNO$: C,66.31; H,3.71; N,5.16 Found: C,65.97; H,3.56; N,5.11.

PREPARATION 24

7-Benzoyl-3-methylindolin-2-one.

A stirred solution of 8 g. (0.027 mole) of 7-benzoyl-3-methyl-3-methylthioindolin-2-one in 80 ml. of tetrahydrofuran was treated under $N_2$ with 40 g. of a commercial Raney nickel-water mixture over a 2 hr. period. At the end of this period the mixture was filtered and the residue washed thoroughly with tetrahydrofuran. One drop of concentrated hydrochloric acid was added to the filtrate and the dark orange solution turned pale yellow. The solution was stripped under vacuum to yellow oil which crystallized on seeding. The material was recrystallized from toluene petroleum ether to give a white crystalline material. The solid (6.0 g., 89% yield) melted at 125°-127° C.

Analysis: Calc'd for $C_{16}H_{13}NO_2$: C,76.43; H,5.22; N,5.57 Found: C,76.38; H,5.22; N,5.52.

PREPARATION 25

7-(4-Fluorobenzoyl)indolin-2-one.

A stirred suspension of 12.3 g. (0.41 mole) of 7-(4-fluorobenzoyl)-3-methylthioindolin-2-one in 250 ml. of tetrahydrofuran was treated over a two hour period with 60 g. of a commercial Raney-nickel water suspension. The mixture was filtered under nitrogen and the residue washed with tetrahydrofuran and methylene chloride. The filtrate was treated with a few drops of conc. hydrochloric acid and concentrated under reduced pressure to give 9.5 g. (91%) of 7-(4-fluorobenzoyl)indolin-2-one.

EXAMPLE 1

2-Amino-5-benzoylphenylacetic Acid.

A mixture of 1.0 g. (0.004 mole) of 5-benzoylindolin-2-one and 30 ml. of 3N sodium hydroxide was refluxed for 0.5 hour. The reaction mixture was cooled, acidified to pH 6 with 3N hydrochloric acid and slightly acidic solution was extracted with chloroform. The chloroform extracts were dried (magnesium sulfate) and concentrated to a solid. Recrystallization from ethanol-water gave 0.9 g. (84.5%) of pure product which melted at 143°-145° C.

Analysis: Calculated for $C_{15}H_{13}NO_3$: C,70.57; N,5.13; N,5.49 Found: C,70.80; N,5.18; N,5.55.

EXAMPLE 2

2-Amino-5-benzoyl-α-methylphenylacetic Acid.

When, in the procedure of Example 1, an equal molar amount of 5-benzoyl-3-methylindolin-2-one is used in place of 5-benzoylindolin-2-one, there is obtained 2-amino-5-benzoyl-α-methylphenylacetic acid.

EXAMPLE 3

2-Amino-3-benzoylphenylacetic Acid.

A mixture of 1.0 g. (0.004 mole) of 7-benzoylindolin-2-one was added to 30 ml. of 3N sodium hydroxide and the basic solution was refluxed for 45 minutes under nitrogen. The mixture was filtered and the filtrate was neutralized with glacial acetic acid. The precipitate was filtered off, washed with water and dried. The material melted at 122° C. (dec.). The yield was 0.8 g. (72%).

Analysis: Calculated for $C_{15}H_{13}N_1O_3$: C,70.58; H,5.13; N,5.49 Found: C,70.36; H,5.11; N,5.48.

EXAMPLE 4

In the same manner as given in Example 1,
2-amino-5-(p-chlorobenzoyl)phenylacetic acid,
2-amino-5-(o-fluorobenzoyl)phenylacetic acid,
2-amino-5-(p-methoxybenzoyl)phenylacetic acid, and
2-amino-5-(m-trifluoromethylbenzoyl)phenylacetic acid are prepared from
5-(p-chlorobenzoyl)indolin-2-one,
5-(o-fluorobenzoyl)indolin-2-one,
5-(p-methoxybenzoyl)indolin-2-one, and
5-(m-trifluoromethylbenzoyl)indolin-2-one.

EXAMPLE 5

In the same manner as given in Example 2,
2-amino-3-(p-chlorobenzoyl)phenylacetic acid,
2-amino-3-(o-fluorobenzoyl)phenylacetic acid, and
2-amino-3-(m-trifluoromethylbenzoyl)phenylacetic acid are prepared from
7-(p-chlorobenzoyl)indolin-2-one,
7-(o-fluorobenzoyl)indolin-2-one, and
7-(m-trifluoromethylbenzoyl)indolin-2-one.

EXAMPLE 6

2-Amino-3-benzoyl-5-chlorophenylacetic Acid Hemihydrate.

A mixture of 1.5 g. (0.055 mole) of 5-chloro-7-benzoylindolin-2-one in 25 ml. of 3N sodium hydroxide was refluxed for 45 min. and the resulting solution filtered and diluted with an equal volume of water. The solution was then neutralized slowly with glacial acetic acid. The resulting yellow-green precipitate was filtered off and dried in a drying pistol (no heat). The compound weighed 1.0 g. (63%) and melted at 85°–87° C.

Analysis: Calc'd for $C_{15}H_{12}ClNO_3 \cdot \frac{1}{2} H_2O$: C,60.31; H,4.39; N,4.69 Found: C,60.59; H,4.09; N,4.65

EXAMPLE 7

Sodium -2-amino-3-benzoyl-5-methoxyphenylacetate Sesquihydrate.

A suspension of 75 mg. (0.27 mole) of 5-methoxy-7-benzoylindolin-2-one in 5 ml. of 3N sodium hydroxide was refluxed for 2.5 hr. The resulting yellow-orange solution was cooled, diluted with several volumes of water, filtered and saturated with sodium chloride. The solution was then passed slowly through a polyethylene column ($\frac{1}{4}$ inch d. × 8 inches long) containing Amberlite XAD-2 polymeric sorbent. The column was then washed with a saturated sodium chloride solution to remove all residual base. While attempting to wash off the sodium chloride, however, the desired product began to elute as well (as noted by following its distinctive yellow color). A number of fractions were collected to insure removal of all the sodium chloride and as the color began to fade from the eluate the column was finally flushed with methanol and acetone. Evaporation of this organic solution yielded (80%) a yellow solid which decomposed above 265° C. and analyzed for 1.5 moles of water as confirmed by the nuclear magnetic resonance spectrum.

Analysis: Calc'd for $C_{16}H_{14}NO_4 \cdot 1\frac{1}{2} H_2O$: C,57.49; H,5.126; N,4.19 Found: C,57.63; H,4.90; N,4.25.

EXAMPLE 8

Sodium 2-amino-3-benzoylphenylacetate Dihydrate.

A mixture of 2.6 g. of (2-amino-3-benzoylphenyl)acetic acid and sodium hydroxide (0.1 mole) in 25 ml. of water was stirred for approximately 10 min. and then heated to reflux under nitrogen. The reaction mixture was then cooled and filtered. The filtrate was evaporated down to approximately 2 ml., refiltered and a large volume of acetone added to the filtrate to precipitate the product as bright yellow flakes. Yield 70%.

Analysis: Calc'd for $C_{15}H_{16}NO_5Na$: C,57.51; H,5.15; N,4.47 Found: C,58.22; H,4.62; N,4.47.

EXAMPLE 9

Ethyl 2-amino-3-benzoylphenylacetate.

A solution of 2.5 g. (0.009 mole) of the sodium salt of 2-amino-3-benzoylphenylacetic acid in 25 ml. of dry dimethylformamide was treated with 5.0 g. (0.035 mole) of ethyl iodide. The mixture was stirred two hours at room temperature using a magnetic stirrer. The mixture was diluted with water and the aqueous solution extracted several times with ethyl ether. The combined extracts were washed with water, dried over sodium sulfate and concentrated under vacuum to a yellow solid. The solid was recrystallized from absolute ethanol to give 1.7 gms. (61.0%) of yellow needles which melted at 77°–78° C.

Analysis: Calc'd for $C_{17}H_{17}NO_3$: C,72.07; H,6.05; N,4.94 Found: C,72.33; H,5.83; N,5.07

EXAMPLE 10

Methyl 2-amino-3-benzoylphenylacetate.

A solution of 4.0 g. (0.014 mole) of the sodium salt of 2-amino-3-benzoylphenylacetic acid in 100 ml. of dry dimethylformamide was treated with 8.0 g. (0.057 mole) of methyl iodide. After stirring for two hours the solution was poured into water and the aqueous solution extracted several times with ethyl ether. The combined extracts were washed with water, dried over sodium sulfate and concentrated under vacuum to a yellow oil. The oil was crystallized from a chilled methanol-water solution to give 3.5 gms. (90%) of a yellow solid which melted at 52°–54° C.

Analysis: Calc'd for $C_{16}H_{15}NO_3$: C,71.36; H,5.61; N,5.20 Found: C,71.51; H,5.63; N,5.27.

EXAMPLE 11

Methyl 2-dimethylamino-3-benzoylphenylacetate.

A stirred solution of 4.6 gms. (0.0165 mole) of methyl 2-amino-3-benzoylphenylacetate and 13.2 ml. (0.165 mole) of 37% formaldehyde in 66 ml. of acetonitrile was treated wih 3.14 gms. (0.0495 mole) of sodium cyanoborohydride. Glacial acetic acid (1.65 ml.) was added over a ten minute period and stirring contained for 2.0 hrs. at room temperature. An additional 1.65 ml. of glacial acetic acid was added and the mixture stirred over a weekend (co. 65 hours). The mixture was diluted with ether and the ether solution was successively washed with 3N potassium hydroxide solution, water, dried over sodium sulfate and concentrated under vacuum to give approximately 1.0 g. (18%) of a yellow oil. A portion of the oil was molecularly distilled for an analytical sample.

Analysis: Calc'd for $C_{18}H_{19}NO_3$: C,72.71; H,6.44; N,4.71 Found: C,72.33; H,6.26; N,4.99.

EXAMPLE 12

2-Dimethylamino-3-benzoylphenylacetic Acid.

A mixture of 500 mg. (1.85 mmole) of methyl 2-dimethylamino-3-benzoylphenylacetate and 15 ml. of 3N sodium hydroxide was refluxed for 1.5 hr. under nitrogen. The cooled filtered reaction mixture was diluted with an equal volume of water and neutralized with glacial acetic acid. The precipitate which formed could not be recrystallized and was therefore dissolved in benzene and placed on a magnesium silicate column. The column was eluted with benzene-acetone to give 300 mg. of product which melted at 144°-146° C. after recrystallization from benzene-isooctane.

Analysis: Calc'd for $C_{17}H_{17}NO_3$: C,72.07; H,6.05; N,4.94 Found: C,72.32; H,6.09; N,4.85.

EXAMPLE 13

Sodium 2-amino-6-benzoylphenylacetate Hydrate.

A suspension of 4.5 g. (0.0190 mole) of 4-benzoylindolin-2-one in 200 ml. of 3N sodium hydroxide was refluxed under a nitrogen atmosphere for 4 hr. The volume of water was reduced by approximately half, and the solution saturated with sodium chloride. The solution was chromatographed on a 230 ml. (wet volume) column of Amberlite XXXX2 ion exchange resin packed in distilled water. The product precipitated on the top of the column packing, but dissolved as the column was eluted with distilled water. The fractions containing the product were collected, combined, and the solvent removed under reduced pressure to give 4.6 g. of solid. Recrystallization from methanol-ether gave 0.91 g. of a yellow solid, m.p. 256.5°-258.5° C. (dec.). The filtrate was evaporated under reduced pressure and the residue was dissolved in hot isopropanol by adding a small amount of water. The hot solution was filtered to remove a suspended solid. The filtrate seeded and placed in the freezer for 12 hr. The pale yellow solid which separated was collected by filtration and yielded 2.84 g. (50.3%) of product, m.p. 254.5°-256° C. (dec.). A portion of the bulk product was dried under high vacuum at room temperature.

Analysis: Calc'd for $C_{15}H_{14}NaNO_4$: C,61.017; H,4.779; N,4.74 Found: C,60.63; H,4.50; N,4.71.

EXAMPLE 14

Sodium 2-amino-3-(4-chlorobenzoyl)phenylacetate Hydrate.

A mixture of 3.5 g. (0.0125 mole) of 2-amino-3-(p-chlorobenzoyl)phenylacetic acid in a water solution containing 0.5 g. of sodium hydroxide (0.125 mole) was refluxed 45 minutes, cooled and filtered. The filtrate was concentrated to an oily consistency and poured into a large volume of acetone. A yellow precipitate separated which was collected and identified by nuclear magnetic resonance spectrum as the desired product. The product (2.6 g.) 67%) melted at 265° C. (dec.) after crystallization from ethanol-ethyl ether.

Analysis: Calc'd for $C_{15}H_{13}ClNO_4Na$: C,54.64; H,3.97; N,4.24 Found: C,55.61; H,3.68; N,4.31

EXAMPLE 15

Sodium 2-amino-3-benzoyl-α-methylphenylacetate Hydrate.

A suspension of 9 g. (0.036 mole) of 7-benzoyl-3-methylindolin-2-one in 100 ml. of 3N sodium hydroxide was refluxed for 18 hrs. under nitrogen. The mixture was filtered and stripped under water pump vacuum to yield a gummy mixture of sodium hydroxide, water, and product. The mixture was triturated with boiling isopropanol and filtered. The isopropanol solution was cooled and filtered to separate the bright yellow product. The product weighed 4.0 g. and melted at 218° C. (dec.)

Analysis: Calc'd for $C_{16}H_{14}NO_3.Na$: C,57.31; H,5.41; N,4.18 Found: C,57.69; H,5.12; N,4.27.

EXAMPLE 16

Potassium 2-amino-3-benzoylphenylacetate Hydrate.

A solution of 4.0 g. (0.015% mole) of 2-amino-3-benzoylphenylacetic acid in 40 ml. of tetrahydrofuran was treated with 5.06 g. (0.045 mole) of 50% potassium hydroxide solution; a precipitate separated immediately. The cold solution (ice bath) was stirred one hour under nitrogen and filtered. The dried product was recrystallized from ethanol-isopropyl ether to give 3.5 g. (72%) of product as long yellow needles.

Analysis: Calc'd for $C_{15}H_{12}NO_3K.H_2O$: C,57.86; H,4.53; N,4.50 Found: C,57.78; N,4.47; N,4.62

EXAMPLE 17

2-Amino-5-(3,4-methylenedioxybenzoyl)phenylacetic Acid.

When, in the procedure of Example 1, an equal molar amount of 5-(3,4-methylenedioxybenzoyl)indolin-2-one is used in place of 5-benzoylindolin-2-one, there is obtained 2-amino-5-(3,4-methylenedioxybenzoyl)phenylacetic acid.

EXAMPLE 18

2-Amino-5-(3,4-dimethoxybenzoyl)phenylacetic Acid.

When, in the procedure of Example 1, an equal molar amount of 5-(3,4-dimethoxybenzoyl)indolin-2-one is used in place of 5-benzoylindolin-2-one, there is obtained 2-amino-5-(3,4-dimethoxybenzoyl)phenylacetic acid.

EXAMPLE 19

2-Amino-5-(3,4-dichlorobenzoyl)phenylacetic Acid.

When, in the procedure of Example 1, an equal amount of 5-(3,4-dichlorobenzoyl)indolin-2-one is used in place of 5-benzoylindolin-2-one, there is obtained 2-amino-5-(3,4-dichlorobenzoyl)phenylacetic acid.

EXAMPLE 20

2-Amino-5-(3-methoxy-4-chlorobenzoyl)phenylacetic Acid.

When, in the procedure of Example 1, an equal molar amount of 5-(3-methoxy-4-chlorobenzoyl)indolin-2-one is used in place of 5-benzoylindolin-2-one, there is obtained 2-amino-5-(3-methoxy-4-chlorobenzoyl)phenyl acetic acid.

The alkali metal salts prepared as described in the examples hereinabove are isolated in hydrated forms. They can be dehydrated under vacuum and maintained in an anhydrous form in the absence of moisture.

EXAMPLE 21

Ethyl 2-amino-3-(4-chlorobenzoyl)phenylacetate.

Fourteen grams of sodium 2-amino-3-(4-chlorobenzoyl) phenylacetate was dissolved in approximately 150 ml. of dimethylformamide and the solution treated with 30 g. of ethyl iodide. The solution was stirred at room temperature for 2.5 hrs., the solution added to water and the mixture extracted several times with benzene. The combined benzene extracts were washed with dilute base and water, dried over sodium sulfate and concentrated to an oil which crystallized on trituration with petroleum ether (30–60). Recrystallization from absolute ethanol gave 11.6 g. of yellow flakes; m.p. 101°–102° C.

Analysis: Calculated for $C_{17}H_{16}ClNO_3$: C,64.26; H,5.08; N,4.41 Found: C,65.14; H,5.06; N,4.51.

EXAMPLE 22

2-Amino-3-(4-fluorobenzoyl)phenylacetic Acid.

A mixture of 1.5 g. (0.006 mole) of 7-(4-fluorobenzoyl) indolin-2-one in 50 ml. of 3N sodium hydroxide was refluxed under nitrogen for 45 min. The solution was cooled, diluted with an equal volume of water, filtered, and the filtrate was extracted two times with 50 ml. of ether. The aqueous basic solution was treated dropwise with glacial acetic acid until a heavy yellow precipitate formed. The precipitate was filtered off, washed thoroughly with water and air-dried. The yield was 1.1 g. (68%); m.p. 136°–137° C.

Analysis: Calculated for $C_{15}H_{12}FNO_3$: C,65.93; H,4.43; N,4.17 Found: C,65.79; H,4.49; N,4.94.

EXAMPLE 23

Sodium 2-amino-3-(4-fluorobenzoyl)phenylacetate Hydrate.

A solution of 1 g. (0.0036 mole) of 2-amino-3-(4-fluorobenzoyl)phenylacetic acid in 10 ml. of tetrahydrofuran was treated with 0.7 g. of a 50% sodium hydroxide solution (0.009 mole) and stirred under nitrogen for 15 min. before a yellow precipitate developed. The stirred mixture was cooled in an ice bath for 2 hr. The precipitate was then filtered off and air-dried. Recrystallization from tetrahydrofuran-water yielded 150 mg. (20%) of product which melted at 240°–250° C. (dec.).

Analysis: Calculated for $C_{15}H_{11}FNO_3.Na.H_{20}$: C,57.51; H,4.18; N,4.47

Found: C,58.23; H,3.81; N,4.53.

EXAMPLE 24

2-Amino-3-(4-methoxybenzoyl)phenylacetic Acid.

A solution of sodium methoxide maintained under nitrogen (2.27 g. of sodium in 25 ml. of methanol) was treated successively with 50 ml. of benzene and 3.4 g. (0.013 mole) of 7-(4-fluorobenzoyl)indolin-2-one. The mixture was refluxed for 4 hr. The mixture was concentrated and the residue was treated with 100 ml. of 3N sodium hydroxide and refluxed under nitrogen for 2 hr. The resulting solution was cooled, diluted with 100 ml. of water and filtered. The filtrate was washed three times with 60 ml. of ether, treated with charcoal and filtered. The filtrate was then treated dropwise with glacial acetic acid giving a yellow precipitate which was filtered off, washed thoroughly with water and air-dried. The yield 2.5 g. (66%); m.p. 117°–118° C.

Analysis: Calculated for $C_{16}H_{15}NO_4$: C,67.36; H,5.30; N,4.91

Found: C,67.25; H,5.18; N,4.99.

EXAMPLE 25

Magnesium 2-amino-3-benzoylphenylacetate Trihydrate.

An aqueous solution of 6.36 g. (0.02 mole) of 2-amino-3-benzoylphenylacetic acid was treated with an aqueous solution of magnesium chloride (0.01 mole). A precipitate formed immediately. After 15 min. of stirring, the bright yellow precipitate was filtered and dried. The yield was 4.06 g. and the salt melted over the broad range of 150°–190° C.

Analysis: Calculated for $C_{30}H_{30}N_2O_9Mg$: C,61.40; H,5.15; N,4.77

Found: C,61.18; H,5.19; N,4.72.

EXAMPLE 26

Calcium-2-amino-3-benzoylphenylacetic Acid Dihydrate.

A stirred solution of 5 g. of sodium 2-amino-3-benzoylphenylacetate hydrate (0.02 mole) in 50 ml. of water was treated with 1.2 g. of calcium chloride (0.01 mole) in 10 ml. of water. An immediate precipitate developed. After an additional 15 min. stirring the precipitate was collected. Recrystallization from ethanol-water gave bright yellow needles which melted over the broad range of 160°–240° C. (dec.).

Analysis: Calculated for $C_{30}H_{28}N_2O_8Ca$: C,60.91; H,4.85; N,4.60

Found: C,60.70; H,4.92; N,4.72.

FORMULATION AND ADMINISTRATION

The present invention also contemplates novel compositions containing the compounds of the invention as active ingredients. Effective quantities of any of the foregoing pharmacologically active compounds may be administered to a living animal body in any one of various ways, for example, orally as in capsules or tablets, parenterally in the form of sterile solutions or suspensions, and in some cases intravenously in the form of sterile solutions. In forming the novel compositions of this invention, the active ingredient is incorporated in a suitable carrier, illustratively, a pharmaceutical carrier. Suitable pharmaceutical carriers which are useful in formulating the compositions of this invention include starch, gelatin, glucose, magnesium carbonate, lactose, malt and the like. Liquid compositions are also within the purview of this invention and suitable liquid pharmaceutical carriers include ethyl alcohol, propylene glycol, glycerine, glucose syrup and the like.

The pharmacologically active compounds may be advantageously employed in a unit dosage of from 0.1 to 150 milligrams. The unit dosage may be given a suitable number of times daily so that the daily dosage may vary from 0.3 to 450 milligrams. Five to 25 milligrams appears optimum per unit dose.

The active agents of the invention may be combined with other pharmacologically active agents, or with buffers, antacids or the like, for administration and the proportion of the active agent in the compositions may be varied widely.

The following are examples of compositions formed in accordance with this invention.

1. Capsules

Capsules of 5 mg., 25 mg., and 50 mg. of active ingredient per capsule are prepared. With the higher amounts of active ingredient, adjustment may be made in the amount of lactose.

| Typical blend for encapsulation | Per capsule, mg. |
|---|---|
| Active ingredient | 5.0 |
| Lactose | 296.7 |
| Starch | 129.0 |
| Magnesium stearate | 4.3 |
| Total | 435.0 mg. |

Additional capsule formulations preferably contain a higher dosage of active ingredient and are as follows.

| Ingredients | Per capsule, mg. |
|---|---|
| Active ingredient | 25.0 |
| Lactose | 306.5 |
| Starch | 99.2 |
| Magnesium stearate | 4.3 |
| Total | 435.0 mg. |

In each case, uniformly blend the selected active ingredient with lactose, starch, and magnesium stearate and encapsulate the blend.

2. Tablets

A typical formulation for a tablet containing 5.0 mg. of active ingredient per tablet follows. The formulation may be used for other strengths of active ingredients by adjustment of weight of dicalcium phosphate.

| | | Per tablet, mg. |
|---|---|---|
| (1) | Active ingredient | 5.0 |
| (2) | Corn starch | 13.6 |
| (3) | Corn starch (paste) | 3.4 |
| (4) | Lactose | 79.2 |
| (5) | Dicalcium phosphate | 68.0 |
| (6) | Calcium stearate | 0.9 |
| | | 170.1 mg. |

Uniformly blend 1, 2, 4 and 5. Prepare 3 as a 10 percent paste in water. Granulate the blend with starch paste and pass the wet mass through an eight mesh screen. The wet granulation is dried and sized through a twelve mesh screen. The dried granules are blended with the calcium stearate and pressed.

3. Injectable — 2% sterile solutions.

| | Per cc. |
|---|---|
| Active ingredient | 20 mg. |
| Preservative, e.g., Chlorobutanol | 0.5% weight/volume |
| Water for injection | q.s. |

Prepare solution, clarify by filtration, fill into vials, seal and autoclave.

Various modifications and equivalents will be apparent to one skilled in the art and may be made in the compounds, compositions, and methods of the present invention without departing from the spirit or scope thereof, and it is therefore understood that the invention is to be limited only by the scope of the appended claims.

What is claimed is:

1. The method for alleviating inflammation in a living animal body with a minimum of undesirable side effects comprising internally administering to said living animal body an effective amount of a compound selected from the group having the formula:

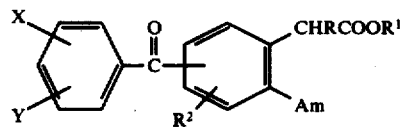

wherein:
R is selected from the group consisting of hydrogen and lower alkyl,
$R^1$ is selected from the group consisting of hydrogen, lower alkyl, sodium and potassium
$R^2$ is selected from the group consisting of hydrogen, halogen having an atomic weight less than 80 and lower alkoxy,
X is selected from the group consisting of hydrogen, lower alkyl, halogen having an atomic weight less than 80, nitro and trifluoromethyl,
Y is selected from the group consisting of hydrogen, lower alkyl, halogen having an atomic weight less than 80, nitro and trifluoromethyl, and
Am is selected from the group consisting of primary amino and dimethylamino.

2. The method of claim 1 wherein the compound is 2-amino-5-benzoylphenylacetic acid.

3. The method of claim 1 wherein the compound is 2-amino-3-benzoyl-5-chlorophenylacetic acid.

4. The method of claim 1 wherein the compound is ethyl-2-amino-3-benzoylphenylacetate.

5. The method of claim 1 wherein the compound is methyl-2-amino-3-benzoylphenylacetate.

6. The method of claim 1 wherein the compound is methyl-2-dimethylamino-3-benzoylphenylacetate.

7. The method of claim 1 wherein the compound is 2-dimethylamino-3-benzoylphenylacetic acid.

8. The method for alleviating inflammation in a living animal body with a minimum of undesirable side effects comprising internally administering to said living animal body an effective amount of 2-amino-3-benzoylphenylacetic acid.

9. The method for alleviating inflammation in a living animal body with a minimum of undesirable side effects comprising internally administering to said living animal body an effective amount of sodium 2-amino-3-benzoyl-5-methoxyphenylacetate sesquihydrate.

10. The method for alleviating inflammation in a living animal body with a minimum of undesirable side effects comprising internally administering to said living animal body an effective amount of sodium 2-amino-3-benzoylphenylacetate dihydrate.

11. The method for alleviating inflammation in a living animal body with a minimum of undesirable side effects comprising internally administering to said living animal body an effective amount of potassium 2-amino-3-benzoylphenylacetate hydrate.

12. A therapeutic composition suitable for alleviating inflammation comprising (a) an effective amount of between about 0.1 and 150 milligrams of a compound selected from the group having the formula:

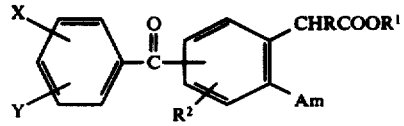

wherein:
R is selected from the group consisting of hydrogen and lower alkyl,
$R^1$ is selected from the group consisting of hydrogen, lower alkyl, sodium and potassium,
$R^2$ is selected from the group consisting of hydrogen, halogen having an atomic weight less than 80, and lower alkoxy,
X is selected from the group consisting of hydrogen, lower alkyl, halogen having an atomic weight less than 80, nitro and trifluoromethyl, Y is selected from the group consisting of hydrogen, lower alkyl, halogen having an atomic weight less than 80, nitro and trifluoromethyl, and Am is selected from the group consisting of primary amino, and dimethylamino, and (b) a pharmaceutically acceptable carrier therefor.

13. The composition of claim 12 wherein the compound is 2-amino-5-benzoylphenylacetic acid.

14. The composition of claim 12 wherein the compound is 2-amino-3-benzoyl-5-chlorophenylacetic acid.

15. The composition of claim 12 wherein the compound is ethyl 2-amino-3-benzoylphenylacetate.

16. The composition of claim 12 wherein the compound is methyl 2-amino-3-benzoylphenylacetate.

17. The composition of claim 12 wherein the compound is methyl 2-dimethylamino-3-benzoylphenylacetate.

18. The composition of claim 12 wherein the compound is 2-dimethylamino-3-benzoylphenylacetic acid.

19. A therapeutic composition suitable for alleviating inflammation comprising (a) an effective amount of between about 0.1 and 150 milligrams of sodium 2-amino-3-benzoylphenylacetic acid and (b) a pharmaceutically acceptable carrier thereof.

20. A therapeutic composition suitable for alleviating inflammation comprising (a) an effective amount of between about 0.1 and 150 milligrams of sodium 2-amino-3-benzoyl-5-methoxyphenylacetate sesquihydrate and (b) a pharmaceutically acceptable carrier thereof.

21. A therapeutic composition suitable for alleviating inflammation comprising (a) an effective amount of between about 0.1 and 150 milligrams of sodium 2-amino-3-benzoyl-phenylacetate dihydrate and (b) a pharmaceutically acceptable carrier thereof.

22. A therapeutic composition suitable for alleviating inflammation comprising (a) an effective amount of between about 0.1 and 150 milligrams of potassium 2-amino-3-benzoylphenylacetate hydrate and (b) a pharmaceutically acceptable carrier thereof.

23. A compound selected from the group having the formula:

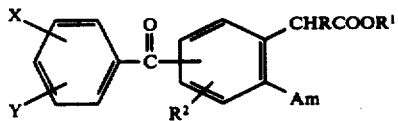

wherein;
R is selected from the group consisting of hydrogen and lower alkyl,
R¹ is selected from the group consisting of hydrogen, lower alkyl, sodium and potassium,
R² is selected from the group consisting of hydrogen, halogen having an atomic weight less than 80, and lower alkoxy,
X is selected from the group consisting of hydrogen, lower alkyl, halogen having an atomic weight less than 80, nitro and trifluoromethyl,
Y is selected from the group consisting of hydrogen, lower alkyl, halogen having an atomic weight less than 80, nitro and trifluoromethyl, and
Am is selected from the group consisting of primary amino (-NH₂) and dimethylamino.

24. The compound of claim 23 which is 2-amino-5-benzoylphenylacetic acid.

25. The compound of claim 23 which is 2-amino-3-benzoyl-5-chlorophenylacetic acid.

26. The compound of claim 23 which is ethyl 2-amino-3-benzoylphenylacetate.

27. The compound of claim 23 whcih is methyl 2-amino-3-benzoylphenylacetate.

28. The compound of claim 23 which is methyl 2-dimethylamino-3-benzoylphenylacetate.

29. The compound of claim 23 which is 2-dimethylamino-3-benzoylphenylacetic acid.

30. A compound selected from the group having the formula:

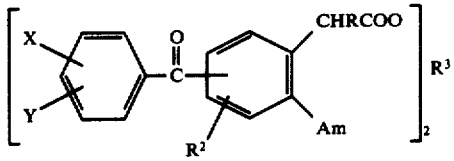

wherein;
R is selected from the group consisting of hydrogen and lower alkyl,
R² is selected from the group consisting of hydrogen, halogen having an atomic weight less than 80 and lower alkoxy,
R³ is selected from the group consisting of calcium and magnesium,
X is selected from the group consisting of hydrogen, lower alkyl, halogen having an atomic weight less than 80, nitro and trifluoromethyl,
Y is selected from the group consisting of hydrogen, lower alkyl, halogen having an atomic weight less than 80, nitro and trifluoromethyl, and
Am is selected from the group consisting of primary amino (—NH₂) and dimethylamino.

31. Calcium 2-amino-3-benzoylphenylacetate dihydrate.

32. Magnesium 2-amino-3-benzoylphenylacetate trihydrate.

33. 2-Amino-3-benzoylphenylacetic acid.

34. Sodium 2-amino-3-benzoyl-5-methoxyphenylacetate.

35. Sodium 2-amino-3-benzoyl-5-methoxyphenylacetate sesquihydrate.

36. Sodium 2-amino-3-benzoylphenylacetate.

37. Sodium 2-amino-3-benzoylphenylacetate dihydrate.

38. Potassium 2-amino-3-benzoylphenylacetate.

39. Potassium 2-amino-3-benzoylphenylacetate hydrate.

40. Sodium 2-amino-3-(p-chlorobenzoyl)phenylacetate hydrate.

41. Ethyl 2-amino-3-(p-chlorobenzoyl)phenylacetate.

42. Sodium 2-amino-3-benzoyl-α-methylphenylacetate hydrate 2.5.

43. 2-Amino-3-(p-fluorobenzoyl)phenylacetic acid.

44. Sodium 2-amino-3-(p-fluorobenzoyl)phenylacetate hydrate.

45. Calcium 2-amino-3-benzoylphenylacetate.

46. Magnesium 2-amino-3-benzoylphenylacetate.

47. 2-Amino-3-(p-methoxybenzoyl)phenylacetic acid.

* * * * *